(12) United States Patent
Dzyubak et al.

(10) Patent No.: US 9,532,750 B2
(45) Date of Patent: Jan. 3, 2017

(54) OBJECT IDENTIFICATION IN DUAL ENERGY CONTRAST-ENHANCED CT IMAGES

(75) Inventors: Oleksandr P. Dzyubak, Rochester, MN (US); Andrew N. Primak, Cleveland, OH (US); Cynthia H. McCollough, Byron, MN (US)

(73) Assignee: MAYO FOUNDATION FOR MEDICAL EDUCATION AND RESEARCH, Rochester, MN (US)

( * ) Notice: Subject to any disclaimer, the term of this patent is extended or adjusted under 35 U.S.C. 154(b) by 1096 days.

(21) Appl. No.: 12/668,703

(22) PCT Filed: Jul. 14, 2008

(86) PCT No.: PCT/US2008/069933
§ 371 (c)(1),
(2), (4) Date: Jul. 21, 2010

(87) PCT Pub. No.: WO2009/012200
PCT Pub. Date: Jan. 22, 2009

(65) Prior Publication Data
US 2010/0278407 A1    Nov. 4, 2010

Related U.S. Application Data

(60) Provisional application No. 60/949,626, filed on Jul. 13, 2007.

(51) Int. Cl.
*G06K 9/00* (2006.01)
*A61B 6/03* (2006.01)
(Continued)

(52) U.S. Cl.
CPC ............... *A61B 6/032* (2013.01); *A61B 6/405* (2013.01); *A61B 6/482* (2013.01); *G06T 5/50* (2013.01);
(Continued)

(58) Field of Classification Search
CPC ......... A61B 6/482; A61B 6/032; A61B 6/405; G06T 7/0012; G06T 2207/10081
(Continued)

(56) References Cited

U.S. PATENT DOCUMENTS 6,721,387 B1   4/2004 Naidu et al.
6,754,298 B2   6/2004 Fessler
(Continued)

OTHER PUBLICATIONS

The International Search Report and Written Opinion as mailed on Jan. 20, 2009 for International Patent Application PCT/US2008/069933.

*Primary Examiner* — Victoria Shumate
*Assistant Examiner* — Reginald R Reyes
(74) *Attorney, Agent, or Firm* — Quarles & Brady, LLP (57) ABSTRACT

Contrast from dual energy CT images is removed without affecting other aspects of the image, including objects surrounded by contrast. Dual energy images are acquired during a study of a subject. First, a binary mask image ("Contrast localizer") is produced to localize the contrast-enhanced areas and build sets of images with contrast-enhanced areas only ("Contrast images") and complement images with contrast-enhanced areas removed ("Contrast complement images") for both low and high x-ray beam energy image sets. Only the contrast images are used for dual energy contrast subtraction. Second binary mask image ("Subject localizer") is produced to localize the objects under study. This mask image is used to reconstruct both low and high energy image sets with contrast selectively removed and subject present.

8 Claims, 10 Drawing Sheets

(51) Int. Cl.
  *A61B 6/00* (2006.01)
  *G06T 5/50* (2006.01)
  *A61B 5/20* (2006.01)

(52) U.S. Cl.
  CPC ............... *A61B 5/201* (2013.01); *A61B 6/481* (2013.01); *G06T 2207/10081* (2013.01)

(58) Field of Classification Search
  USPC ........................................................ 382/131
  See application file for complete search history.

(56) References Cited

U.S. PATENT DOCUMENTS

| | | |
|---|---|---|
| 6,816,564 B2 | 11/2004 | Charles et al. |
| 7,031,426 B2 | 4/2006 | Iatrou et al. |
| 2003/0215120 A1* | 11/2003 | Uppaluri et al. ............. 382/128 |
| 2004/0131117 A1* | 7/2004 | Sheraizin ............. H04N 19/105 375/240.12 |
| 2007/0092056 A1* | 4/2007 | Flohr .................... A61B 6/032 378/4 |
| 2007/0242802 A1* | 10/2007 | Dafni .................. A61B 6/4233 378/98.11 |
| 2008/0013672 A1* | 1/2008 | Krauss et al. .................... 378/4 |
| 2008/0187094 A1* | 8/2008 | Stodilka ................ A61B 6/032 378/22 |
| 2008/0312884 A1* | 12/2008 | Hostettler et al. ................ 703/2 |

\* cited by examiner

OBJECT IDENTIFICATION IN DUAL ENERGY CONTRAST-ENHANCED CT IMAGES

CROSS-REFERENCE TO RELATED APPLICATIONS

This application claims priority to PCT International Application No. PCT/US2008/069933 filed on Jul. 14, 2008, which claims priority to U.S. Provisional Patent Application No. 60/949,626 filed on Jul. 13, 2007, which is hereby incorporated by reference herein in its entirety.

BACKGROUND OF THE INVENTION

The present invention relates to computed tomography (CT) imaging apparatus; and more particularly, contrast-enhanced images acquired at more than one x-ray energy level.

In a current computed tomography system, an x-ray source projects a fan-shaped beam which is collimated to lie within an X-Y plane of a Cartesian coordinate system, termed the "imaging plane." The x-ray beam passes through the object being imaged, such as a medical patient, and impinges upon an array of radiation detectors. The intensity of the transmitted radiation is dependent upon the attenuation of the x-ray beam by the object and each detector produces a separate electrical signal that is a measurement of the beam attenuation. The attenuation measurements from all the detectors are acquired separately to produce the transmission profile.

The source and detector array in a conventional CT system are rotated on a gantry within the imaging plane and around the object so that the angle at which the x-ray beam intersects the object constantly changes. A group of x-ray attenuation measurements from the detector array at a given angle is referred to as a "view" and a "scan" of the object comprises a set of views made at different angular orientations during one revolution of the x-ray source and detector. In a 2D scan, data is processed to construct an image that corresponds to a two dimensional slice taken through the object. The prevailing method for reconstructing an image from 2D data is referred to in the art as the filtered backprojection technique. This process converts the attenuation measurements from a scan into integers called "CT numbers" or "Hounsfield units", which are used to control the brightness of a corresponding pixel on a display.

Dual source CT systems have two separate x-ray sources and associated detector arrays, which rotate together in the gantry during a scan. The x-ray sources may be operated at different energy levels to acquire two image data sets from which a low energy and a high energy image may be reconstructed.

Figure 3:
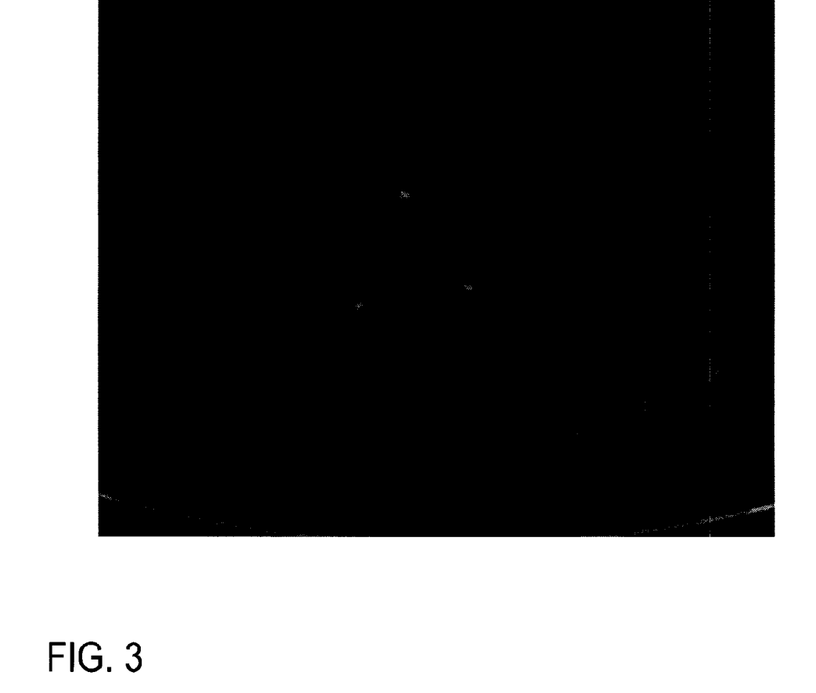
FIG. 3 is an image produced by a conventional dual energy subtraction method.

Proper calibration of image pixel values versus x-ray beam energy can be used for qualitative and quantitative material composition evaluation of a scanned object. The ratio of CT numbers at high and low energies can be calculated for a given material and later be used to selectively remove this material from the image. The ratio is calculated using mean pixel value over the area of the material being removed. For this reason, the subtraction of a material leaves residual pixels with comparatively low values. Such a procedure is called "dual energy image subtraction" and the result of using a conventional method is shown in FIG. 3. In this conventional method pixel values of two corresponding images acquired at different x-ray beam energies are subtracted from each other using a ratio calculated for one particular material. Thus, the particular material, or tissue type, is removed from the subtracted images, but the resulting image has poor quality and severely degraded intensity levels over the entire image. In addition, the brightness in the final subtraction images is no longer measured in Hounsfield units.

SUMMARY OF THE INVENTION

The present invention is a method for removing a selected tissue type, or material, from a CT image, and particularly, a method which removes the signal produced by contrast agent to reveal underlying objects while maintaining the image contrast and indicating pixel values in Hounsfield units.

The acquired high and low energy images are segmented to provide images that depict contrast agent and contrast complement images that depict everything except contrast agent. A dual energy subtraction is employed with the high and low energy contrast images to remove the contrast signal from them. A subject mask is produced from the result and this is used to segment pixels that depict the underlying object of interest in the acquired images. These segmented pixels are then added to the high and low energy contrast complement images to form the final images.

DETAILED DESCRIPTION OF THE PREFERRED EMBODIMENT

Figure 1:
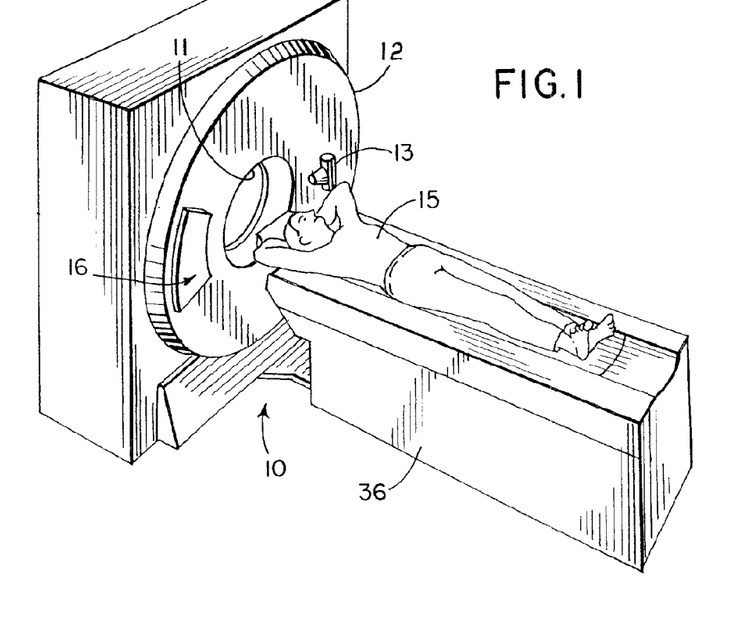
FIG. 1 is a pictorial view of a CT imaging system in which the present invention may be employed.
Figure 2:
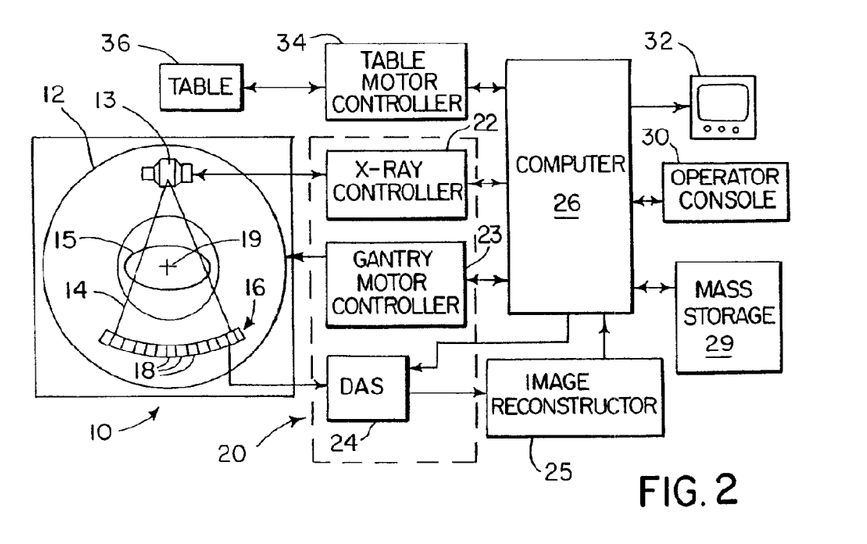
FIG. 2 is a block schematic diagram of the CT imaging system.

With initial reference to FIGS. 1 and 2, a computed tomography (CT) imaging system 10 includes a gantry 12 representative of a "third generation" CT scanner. Gantry 12 has a pair of x-ray sources 13 that each project a fan beam or cone beam of x-rays 14 toward a detector array 16 on the opposite side of the gantry. The detector array 16 is formed by a number of detector elements 18 which together sense the projected x-rays that pass through a medical patient 15. Each detector element 18 produces an electrical signal that represents the intensity of an impinging x-ray beam and hence the attenuation of the beam as it passes through the patient. During a scan to acquire x-ray projection data, the gantry 12 and the components mounted thereon rotate about a center of rotation 19 located within the patient 15 to acquire attenuation data for each of the two x-ray sources.

The rotation of the gantry and the operation of the x-ray sources 13 are governed by a control mechanism 20 of the CT system. The control mechanism 20 includes an x-ray controller 22 that provides power and timing signals to the x-ray sources 13 and a gantry motor controller 23 that controls the rotational speed and position of the gantry 12. A data acquisition system (DAS) 24 in the control mechanism 20 samples analog data from detector elements 18 in each detector array and converts the data to digital signals for subsequent processing. An image reconstructor 25, receives sampled and digitized x-ray data from the DAS 24 and performs high speed image reconstruction. The reconstructed image is applied as an input to a computer 26 which stores the image in a mass storage device 29.

The computer 26 also receives commands and scanning parameters from an operator via console 30 that has a keyboard. An associated display 32 allows the operator to observe the reconstructed image and other data from the computer 26. The operator supplied commands and parameters are used by the computer 26 to provide control signals and information to the DAS 24, the x-ray controller 22 and the gantry motor controller 23. In addition, computer 26 operates a table motor controller 34 which controls a motorized table 36 to position the patient 15 in the gantry 12.

The preferred embodiment of the invention is embodied in a CT urogram procedure in which images are produced of the kidneys and urinary tract to detect kidney stones, evaluate vascular and renal parenchyma and visualize lesions. To perform all these functions with a conventional dual-energy CT scan requires a CT scan without contrast agent and a contrast-enhanced CT scan. By using the present invention all of these functions can be performed with a single, dual energy, contrast-enhanced CT scan.

Figure 4:
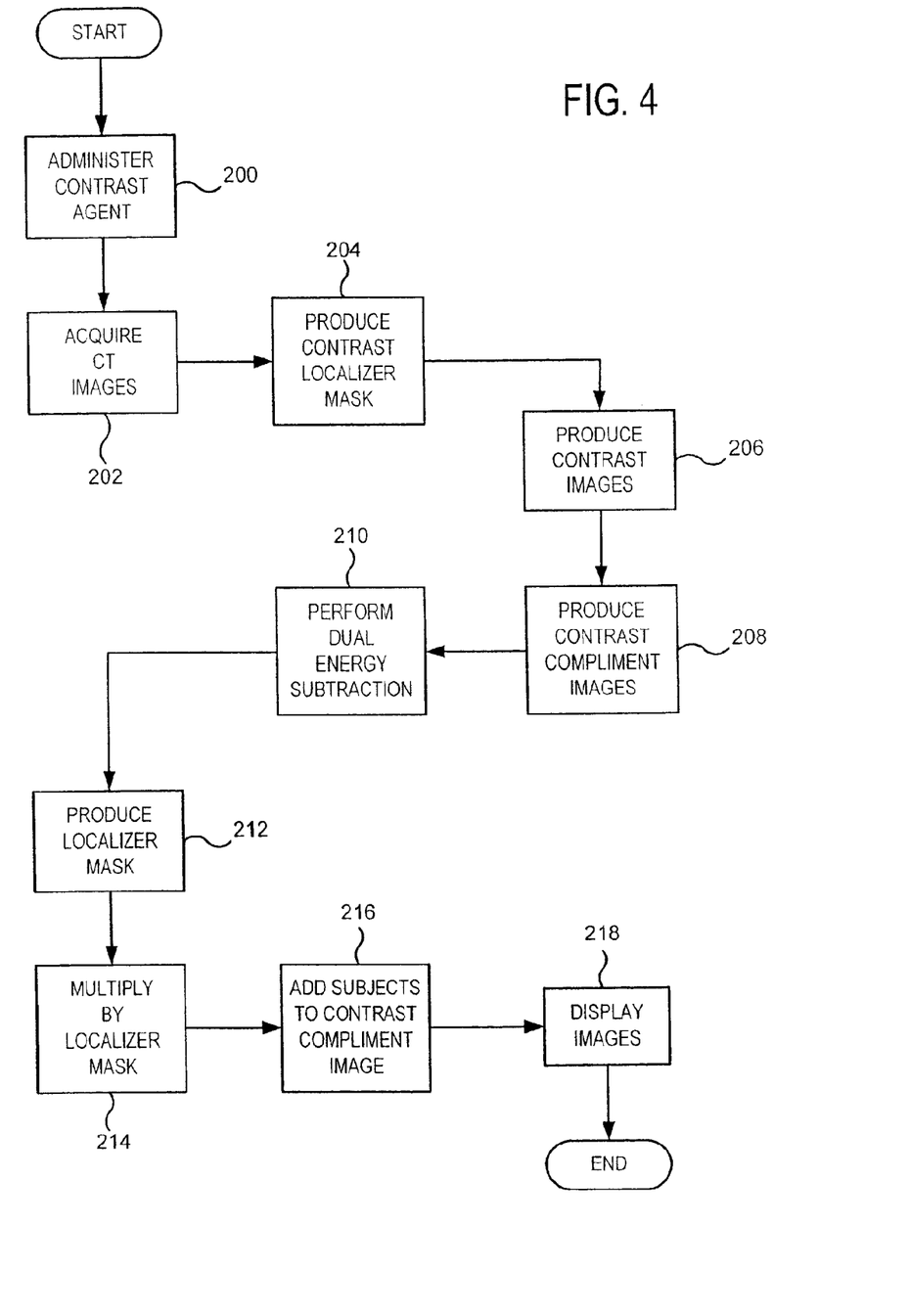
FIG. 4 is a flow chart of the steps performed when practicing a preferred embodiment of the invention on the CT system of FIGS. 1 and 2.
Figure 5A:
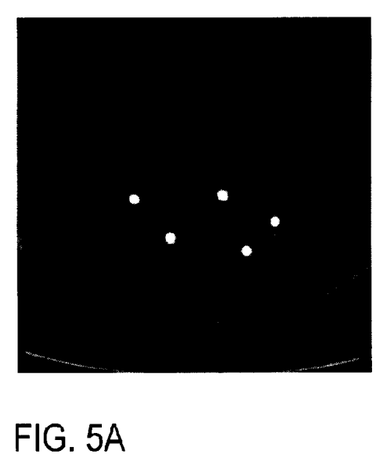
FIGS. 5a and 5b are contrast enhanced images acquired at two energy levels.
Figure 5B:
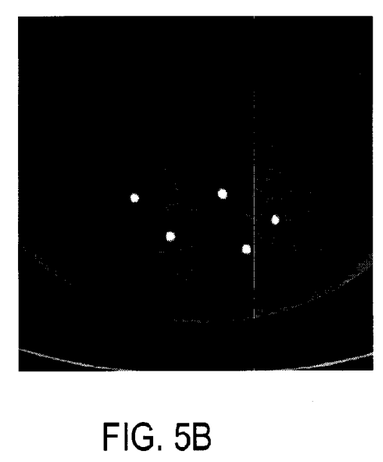

Referring particularly to FIG. 4, the first step indicated by process block 200 is to administer a contrast agent to the subject being examined. An iodine/water solution is used having a known CT number ranging from 500 to 2300 HU at an x-ray energy of 120 kV. As indicated at process block 202, contrast-enhanced CT images are then acquired at two energy levels: 80 kV; and 140 kV during a single scan. A low energy CT image and a high energy CT image are reconstructed from the two acquired data sets and are illustrated in FIGS. 5*a* and 5*b* respectively.

Figure 6:
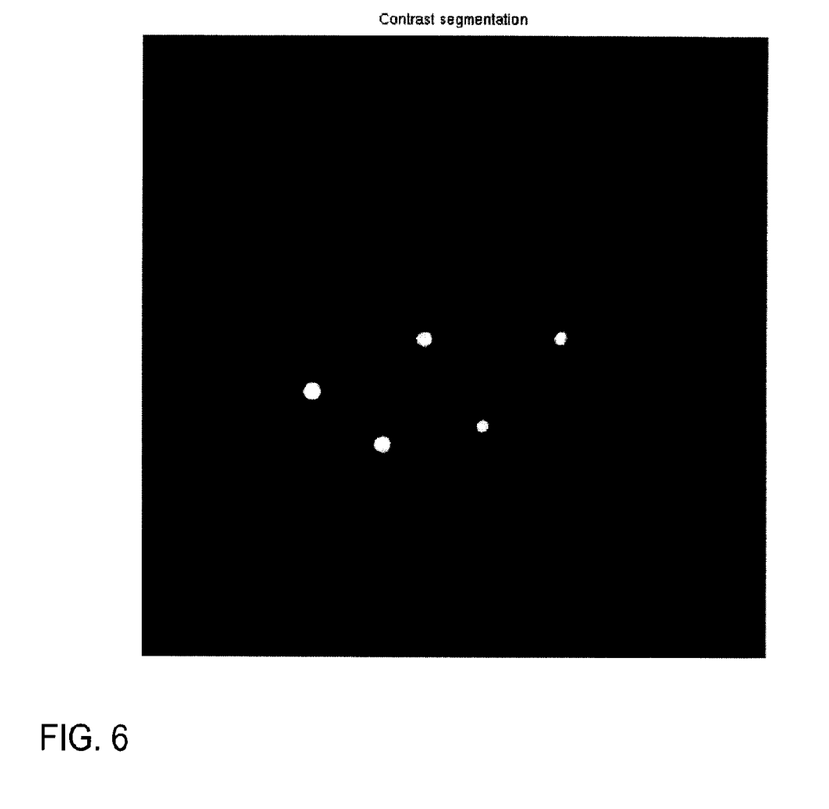
FIG. 6 is an image with only contrast enhanced pixels presented.

A contrast localizer binary mask is produced from these images as indicated at process block 204 and is used to segment the acquired low energy and high energy images. Areas in the acquired images containing contrast agent are easily distinguished and the corresponding image pixels are set to "1" and all other pixels are set to "0". Using this mask, a high energy contrast image and a low energy contrast image are produced as indicated at process block 206. This is accomplished by multiplying each pixel value in the acquired low energy and high energy images by the corresponding pixel values ("1" or "0") in the contrast mask. A resulting contrast image is illustrated in FIG. 6, which depicts all pixels that include contrast agent at their voxel locations.

Figure 7:
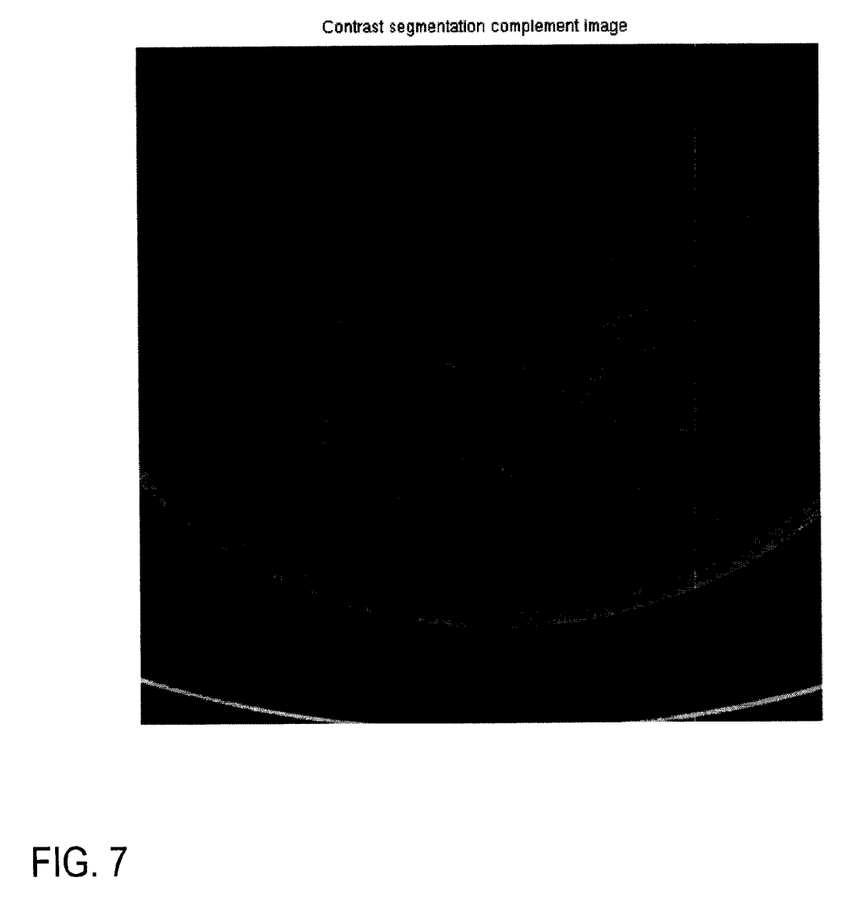
FIG. 7 is an image with contrast enhanced pixels removed.

Similarly, as indicated at process block 208, a high energy contrast complement image and a low energy contrast complement image are produced. This is achieved by first inverting all the pixel values in the contrast localizer mask and then multiplying the two acquired images by the inverted mask. A contrast complement image is illustrated in FIG. 7, which depicts all the pixels that do not include contrast agent at their voxel locations.

Figure 8:
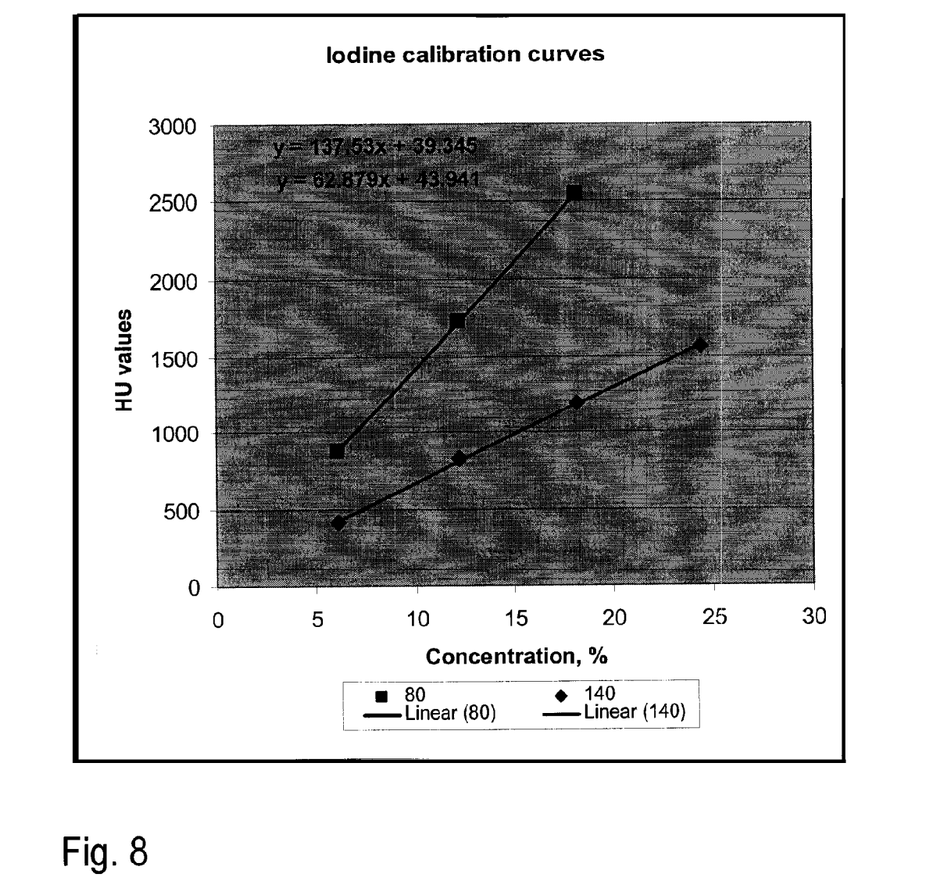
FIG. 8 is a graphic representation of iodine calibration curves.
Figure 9:
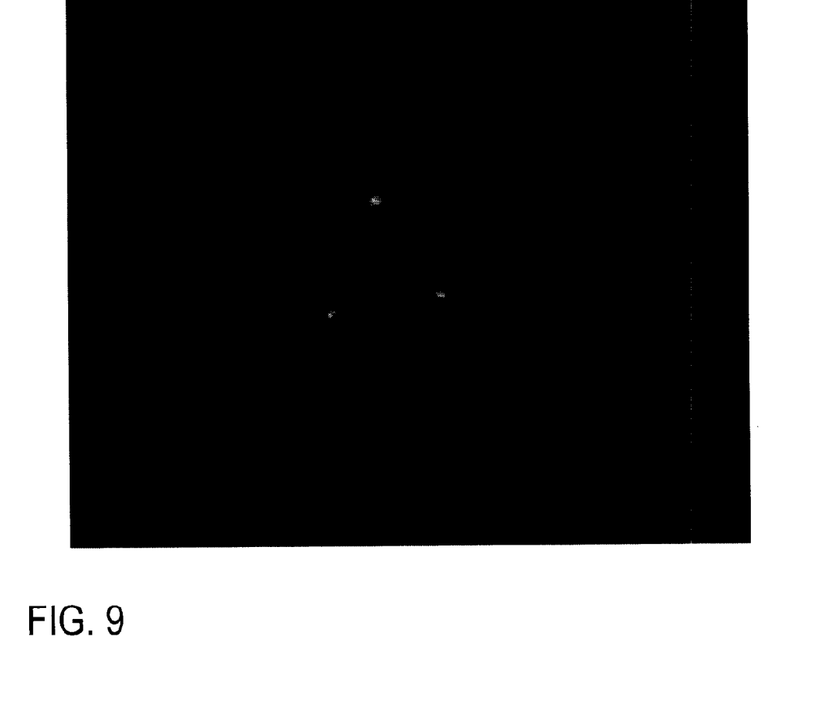
FIG. 9 is an image after dual energy subtraction.

The next step as indicated at process block 210 is to perform a dual energy image subtraction of the high and low contrast images. As shown in FIG. 8, the known iodine concentration is used to determine the relative pixel intensity in these two images and from this a ratio is determined and used to multiply the pixel values in one of the images. As a result, the contrast agent intensity appears the same in both contrast images and their subsequent subtraction effectively removes the iodine contrast from the dual energy subtraction image. Such an image is illustrated in FIG. 9, where the bright pixels indicate the location of underlying objects (e.g., kidney stones) that were previously surrounded by contrast agent and effectively obliterated in the acquired CT images.

Figure 10:
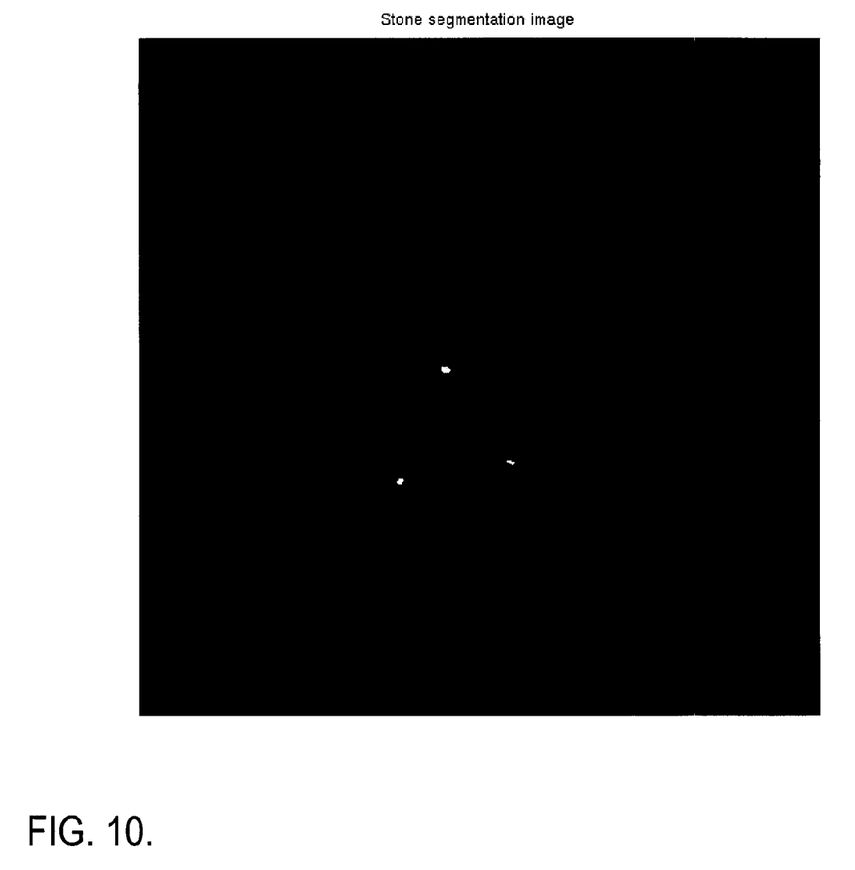
FIG. 10 is a subject localizer mask image.

Using the dual energy subtraction image (FIG. 9) a subject localizer binary mask is then produced as indicated at process block 212. The pixels having higher values are easily segmented and these are set to "1" while the remaining pixels are set to "0". Such a localizer mask is illustrated in FIG. 10.

Figure 11:
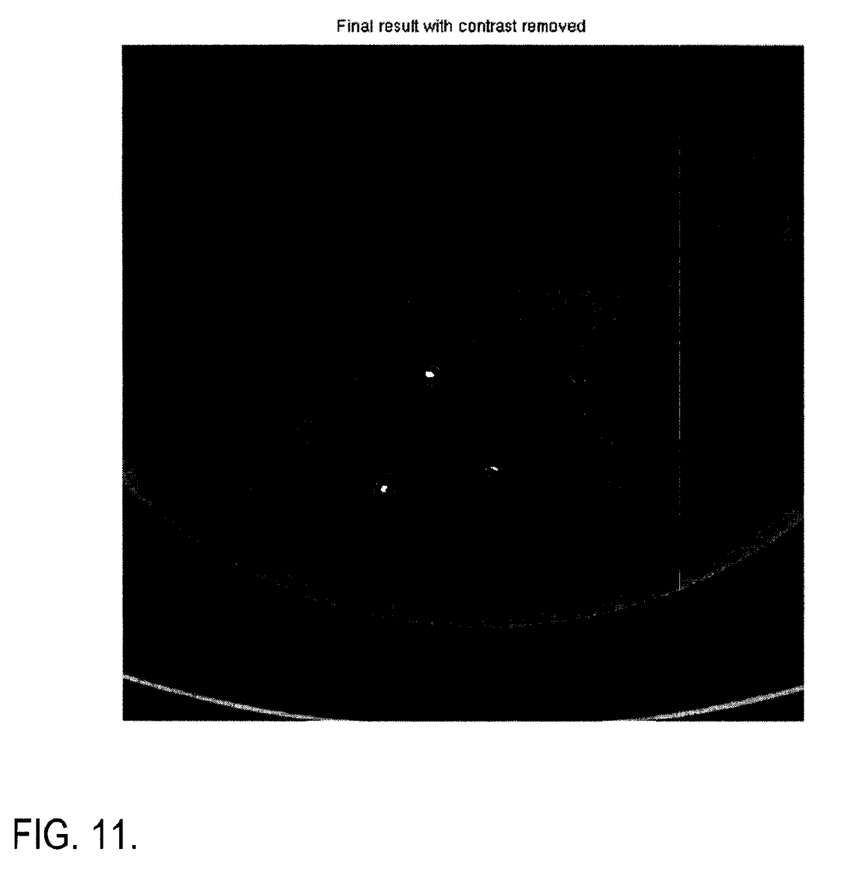
FIG. 11 is a final image with contrast enhanced image pixels removed.

The next step as indicated at process block 214 is to multiply each of the originally acquired low energy and high energy CT images by the subject localizer mask. This produces low and high energy images that depict only the subjects (e.g., kidney stones, plaque, etc.). The final processing step is then to combine these low and high energy subject images with the corresponding low and high energy contrast complement images (FIG. 7) as indicated at process block 216. The final low energy and high energy images illustrated in FIG. 11 reveal the subjects previously obliterated by contrast agent in the surrounding tissues. These images are displayed at process block 218, and the intensity of the pixel values in these images correspond to the original measured Hounsfield numbers despite the dual energy subtraction process.

The invention claimed is:

1. A method for removing contrast enhanced regions from acquired dual energy contrast-enhanced CT images, the steps comprising:
   a) segmenting the acquired dual energy CT images into high and low energy contrast images and contrast complement images;
   b) performing a dual energy subtraction of the high and low energy contrast images to yield a dual energy subtraction image, wherein a null signal is produced by the contrast agent;
   c) producing a subject localizer mask from the dual energy subtraction image identifying pixel locations of a subject;
   d) multiplying an acquired image by the subject localizer mask to produce an image of the subject; and
   e) combining the image of the subject with a contrast complement image.

2. The method of claim 1 in which the step d) is performed on both acquired images and step e) is performed with both subject images and both corresponding contrast complement images.

3. The method as recited in claim 1 in which the subject is a kidney stone.

4. The method as recited in claim 1 in which step c) includes;
   c)i) determining the ratio of the contrast agent signal in the high energy and low energy images;
   c)ii) multiplying one of the contrast images by the ratio; and
   c)iii) subtracting the multiplied contrast image and the other contrast image.

5. The method as recited in claim 4 in which the contrast agent includes iodine and the ratio is determined by the concentration of iodine in the contrast agent.

6. The method of claim 1 in which the step a) further comprises determining a contrast localizer mask and an inverted contrast localizer mask using the acquired dual energy CT images.

7. The method as recited in claim 6, wherein segmenting the acquired dual energy CT images includes multiplying the high and low energy contrast images by the contrast localizer mask to produce the high and low energy contrast images.

8. The method as recited in claim 6, wherein segmenting the acquired dual energy CT images includes multiplying the high and low energy contrast images by the inverted contrast localizer mask to produce the contrast complement images.

* * * * *